(12) United States Patent
Paufique

(10) Patent No.: US 11,452,686 B2
(45) Date of Patent: Sep. 27, 2022

(54) **COSMETIC ACTIVE SUBSTANCE OBTAINED THROUGH BIOCONVERSION BY *LACTOBACILLUS ARIZONENSIS* OF ITS ORIGINAL SUBSTRATE, METHOD FOR OBTAINING SAME COMPOSITION COMPRISING SAME, AND USES**

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

(21) Appl. No.: 17/008,810

(22) Filed: Sep. 1, 2020

(65) Prior Publication Data

US 2021/0059929 A1    Mar. 4, 2021

(30) Foreign Application Priority Data

Sep. 2, 2019 (FR) ................................. FR 1909628

(51) Int. Cl.
| | |
|---|---|
| *A61K 36/00* | (2006.01) |
| *A61K 8/99* | (2017.01) |
| *A61K 8/9789* | (2017.01) |
| *A61K 8/34* | (2006.01) |
| *A61K 8/365* | (2006.01) |
| *A61K 8/64* | (2006.01) |
| *A61K 8/73* | (2006.01) |
| *A61Q 17/00* | (2006.01) |
| *A61Q 19/00* | (2006.01) |
| *A61Q 19/08* | (2006.01) |

(52) U.S. Cl.
CPC ................ *A61K 8/99* (2013.01); *A61K 8/345* (2013.01); *A61K 8/365* (2013.01); *A61K 8/64* (2013.01); *A61K 8/73* (2013.01); *A61K 8/9789* (2017.08); *A61Q 17/005* (2013.01); *A61Q 19/007* (2013.01); *A61Q 19/08* (2013.01); *A61K 2236/11* (2013.01); *A61K 2236/30* (2013.01)

(58) Field of Classification Search
CPC .............................. A61K 35/747; A61Q 19/00
See application file for complete search history.

(56) References Cited

U.S. PATENT DOCUMENTS

| | | | |
|---|---|---|---|
| 2003/0186401 A1 | 10/2003 | Yong-Chul et al. | |
| 2004/0137091 A1* | 7/2004 | Bassi | A61Q 19/08 |
| | | | 424/757 |

FOREIGN PATENT DOCUMENTS

| | | |
|---|---|---|
| EP | 3219304 A1 | 9/2017 |
| JP | 2002191387 A1 | 7/2002 |

OTHER PUBLICATIONS

Swezey et al, *Lactobacillus arizonensis* sp. nov., isolated from jojoba meal. International journal of systematic and evolutionary microbiology, (Sep. 2000) vol. 50 Pt 5, pp. 1803-1809 (Year: 2000).*

Van Boven, Identification of 4,5-didemethyl-4-O-alpha-D-glucopyranosylsimmondsin and pinitol alpha-D-galactosides in jojoba seed meal (*Simmondsia chinensis*). Journal of agricultural and food chemistry, (Sep. 2001) vol. 49, No. 9, pp. 4278-4283 (Year: 2001).*

* cited by examiner

*Primary Examiner* — Qiuwen Mi
(74) *Attorney, Agent, or Firm* — Greer, Burns & Crain, Ltd.

(57) ABSTRACT

The invention relates to a particular cosmetic active substance that is constituted through bioconversion by *Lactobacillus arizonensis* of its original substrate, *Simmondsia chinens*. The invention also relates to a preparation method, to compositions comprising same, and to uses thereof for cosmetic applications.

19 Claims, No Drawings

COSMETIC ACTIVE SUBSTANCE OBTAINED THROUGH BIOCONVERSION BY *LACTOBACILLUS ARIZONENSIS* OF ITS ORIGINAL SUBSTRATE, METHOD FOR OBTAINING SAME COMPOSITION COMPRISING SAME, AND USES

CROSS-REFERENCE TO RELATED APPLICATIONS

This application claims priority to French patent application FR 1909628, filed Sep. 2, 2019.

TECHNICAL FIELD

The invention relates to a cosmetic active substance comprising a supernatant of *Lactobacillus arizonensis* obtained through bioconversion by this bacterium of its original substrate. The invention also relates to the method for obtaining such an active substance, to the cosmetic compositions comprising same, and to the cosmetic uses of this active substance and of these compositions.

PRIOR ART

Dry skin is a common disorder that affects men and women equally. It is accompanied by various symptoms, including discomfort (tightness, itching), excessive scaling, and the appearance of unsightly irregularities (plaques, cracking, etc.). Arms and hands are areas particularly prone to this type of inconvenience.

The purpose of the epidermis, the outermost layer of the skin, is to ensure hydration. Its ability to prevent dehydration depends on various parameters, including:
  its composition in terms of proteins (filaggrin) and lipids.
  the establishment of intercellular junctions (claudin, desmoglein) in order to obtain a cohesive structure.

It is during the process of epidermal differentiation that the protein and lipid skeletons are synthesized. The keratinocytes of the basal layer of the epidermis thus initiate a maturation mechanism that results in migration to the surface of the skin. This step is accompanied by a deep restructuring of the cell structure, the formation of an impermeable lipid cement, and a protein framework that imparts strength and resistance to the epidermis. Beyond the mechanical properties that it confers, filaggrin, an essential element of the protein framework, actively participates in the hydration of the skin due to its status as a precursor to the formation of natural hydration factors. The proper progression of the differentiation process results in the establishment of a barrier function, ensuring the skin's "water capital." Under a constant onslaught from the environment, the functionality of this barrier is maintained thanks to its continuous renewal.

For many years, research on skin has focused on the mechanisms involved in the proper functioning of the epidermis. Among very recent approaches, the influence of skin flora on the integrity of the barrier has been the subject of several studies. In dermatology, for instance, probiotics are described for their ability to improve certain disorders such as psoriasis or atopic dermatitis, but there is currently no satisfactory product for regulating the skin microbiota, improving the renewal of the epidermal barrier, and activating the innate immune defenses.

It is therefore the object of the invention to satisfy this need by providing a cosmetic active substance which, when applied to healthy skin:
  respects the skin microbiota, meaning that it does not have an effect on the diversity and distribution of bacterial communities,
  increases the integrity of the epidermal barrier, particularly by improving the synthesis of the protein framework, by promoting the cohesion of the epidermis and by optimizing the formation of lipid cement,
  activates the renewal of the skin barrier, particularly by increasing the rate of renewal of the epidermis,
  optimizes immunity, particularly by improving the immune barrier of the skin.

To achieve this, the invention relates to a cosmetic active substance obtained through bioconversion by *Lactobacillus arizonensis* of its original substrate, *Simmondsia chinensis*.

SUMMARY OF THE INVENTION

The invention therefore relates to a cosmetic postbiotic.

Over the past decade, scientists have made great strides in understanding the role that microbial flora plays in our health. Most of the work has been done at the intestinal level. On the one hand, these studies have led to a better understanding of the evolution of the microbiota in various contexts, whether physiological or pathological, and, on the other hand, they have led to the emergence of new therapeutic strategies. Several approaches have thus emerged while giving birth to the concept of probiotics in the process. Probiotics are defined as living microorganisms the administration of which in adequate quantities confers health benefits. For a long time, the effect of these bacteria on health was considered to be inseparable from their viability. However, this theory now seems to be evolving in favor of the concept of postbiotics, which correspond to the bioactive metabolites that are produced by probiotics.

The influence of postbiotics on the quality of the skin has not been described and, surprisingly, according to the invention, a cosmetic active substance obtained through bioconversion by at least one *lactobacillus* of at least one of the substrates of said *lactobacillus*—that is, a postbiotic consisting of bioactive metabolites produced by lactobacilli cultured in the presence of their natural substrates—exhibits a cosmetic effect on healthy skin, particularly a moisturizing effect on the skin.

The invention relates specifically to a cosmetic active substance which is characterized in that it is the product obtained through bioconversion by *Lactobacillus arizonensis* of *Simmondsia chinensis*, with *Lactobacillus arizonensis* being a bacterium that is isolated from *Simmondsia chinensis*, and with *Simmondsia chinensis* constituting its original substrate.

The invention also relates to a method for obtaining such an active substance as well as to compositions comprising at least 0.1% by weight of such an active substance.

The active substance according to the invention and the compositions comprising same are particularly useful for cosmetic applications on healthy skin for improving the beauty of the skin, particularly for improving the glow of the skin and/or enhancing the radiance of the skin and/or increasing the hydration of the skin. The invention therefore also relates to the cosmetic use of an active substance according to the invention or of a composition comprising same, as well as to a method for the cosmetic treatment of healthy skin.

Other features of the invention will become apparent from the detailed description that follows.

DETAILED DESCRIPTION OF THE INVENTION

Definitions

In terms of the invention, the expression "cosmetic active substance" or "active substance" is understood to refer to at least one molecule, preferably a set of molecules, having a cosmetic effect on the skin, particularly on the skin cells.

Within the meaning of the invention, "bioconversion" refers to the transformation of the molecules of a plant into one or more other molecules through the action of living organisms such as a *lactobacillus*, for example.

In terms of the invention, "original substrate of a *lactobacillus*" is understood to refer to the plant on which the *lactobacillus* has been isolated and identified.

Active Substance According to the Invention

The invention relates to a cosmetic active substance which is characterized in that it is the product obtained through bioconversion by *Lactobacillus arizonensis* of the original substrate of said *lactobacillus*.

Preferably, the invention relates to a cosmetic active substance which is characterized in that it is the product obtained through bioconversion of *Simmondsia chinensis* (jojoba) by *Lactobacillus arizonensis*. In fact, by using an extract of *Simmondsia chinensis* as a substrate of *Lactobacillus arizonensis*, it is possible to have biomimicry that is close to the natural environment of *Lactobacillus arizonensis*.

Very preferably, the active substance is obtained from the supernatant obtained through bioconversion by *Lactobacillus arizonensis* of *Simmondsia chinensis*, meaning that the active substance consists in whole or part of the—preferably filtered—supernatant that is obtained through bioconversion by *Lactobacillus arizonensis* of *Simmondsia chinensis*.

The ability of the bacterium to produce postbiotics depends on its metabolism. It is therefore essential to calibrate one fundamental parameter: the nature of the nutrient inputs. The invention therefore consists in enriching the culture medium of *lactobacillus* (particularly of *Lactobacillus arizonensis*) with an extract of one of its original substrates (particularly of jojoba or *Simmondsia chinensis* for *Lactobacillus arizonensis*) in order to reproduce its natural environment and encourage it to produce the metabolites necessary for its survival and adaptation. Advantageously, the metabolites produced by this strain have a cosmetic effect on healthy skin and, in particular, can aid in the treatment of dryness in healthy skin.

The active substance according to the invention preferably comprises sugars. The sugar content in the extract can be determined using the DUBOIS method (Dubois M. et al., Analytical chemistry, 28, 3, 350-356, 1956). The total sugar content of the active substance is expressed as a percentage relative to the dry material. The active substance contains between 1 to 5% of sugars by weight relative to the dry material.

The simple-sugar composition of the carbohydrate fraction of the active substance is determined by ionic liquid chromatography, and the size of the molar masses is determined by HPLC with IR detection. It is preferably composed of glucose, fructose, and galactose.

These saccharides preferably consist of molecules with a molar mass ranging from 360 to 13,860 Da.

Preferably, the active substance according to the invention comprises at least one cyclic polyol, and even more preferably it comprises at least Pinnitol. Cyclic polyols, and in particular Pinnitol, participate in the cosmetic activity of the active substance according to the invention. The content of cyclic polyols and particularly of Pinnitol is preferably measured by high pressure liquid phase chromatography coupled to a mass spectrophotometer using a calibration curve with a standard: Commercial D-Pinnitol, produced between 1 and 1000 ppm.

In addition to cyclic polyols and/or sugars, the active substance according to the invention can comprise other molecules. In particular, it can comprise mineral ash and/or proteins. The mineral ash content can be determined by weighing the residues from the incineration of the samples of the active substance according to the invention at 550° C. in an electric muffle furnace. Preferably, the active substance according to the invention has an ash content of between 24% to 33% by weight of dry material of the active substance. The content of proteins can be determined using the LOWRY method (Lowry et al., Protein measurement with the folin reagent, J. Biol. Chem., 193, 265, 1951) or by assaying the total nitrogen using the KJELDHAL method (reference: Official method of analysis of the A.O.C., 12th ed. W Horwitz, E.D., New York, 15-60, 1975). Preferably, the active substance according to the invention has a protein content of between 5 and 13% by weight of dry material, preferably as determined using the Kjeldhal method.

The lactic acid content can be determined by ionic liquid chromatography using a calibration range prepared from a commercial standard. Lactic acid is in the form of sodium lactate when the pH of the solution containing it is greater than its pKa of 3.8. Therefore, the active substance according to the invention preferably has a pH of 5.4 and a sodium lactate content of between 52 and 85%.

The active substance according to the invention can be in liquid form. In this case, it can be supplemented by at least one stabilizer and/or one preservative.

Preferably, when it is in liquid form, the dry material content of the active substance according to the invention is between 50 and 150 g/l, preferably between 70 and 105 g/l.

The liquid form preferably contains 1 to 5% of sugars, 52 to 85% of sodium lactate, 24 to 33% of mineral ash, and 5 to 13% of proteins, the percentages being given by weight of dry material. In liquid form, it can be beige to yellow in color. However, it can be bleached using standard techniques in the field.

The active substance according to the invention can be in solid form, particularly in the form of a powder. In this case, it is preferably constituted by the product of the bioconversion of the substrate by the *lactobacillus* according to the invention and by a support such as maltodextrin, for example. Preferably, the product of the bioconversion represents 10 to 50% by weight of the active substance, and the support from 50 to 90%. The powder form therefore preferably contains 50 to 91% of sugars, 5 to 43% of sodium lactate, 2 to 17% of ash, and 0.5 to 6.5% of proteins, the percentages being given by weight of the active substance comprising a maltodextrin support.

Method for Obtaining the Active Substance According to the Invention

The active substance according to the invention can be obtained by any type of process for bioconversion of at least one substrate by *Lactobacillus arizonensis*.

According to a preferred embodiment, the invention relates to a method for obtaining an active substance according to the invention comprising the implementation of the following steps:

culturing of *Lactobacillus arizonensis* in a culture medium supplemented with *Simmondsia chinensis*, stopping the culture by thermal inactivation separating the biomass from the supernatant by any technique known to those skilled in the art, for example by centrifugation, filtration, or decantation preferably filtering the supernatant to obtain a liquid comprising the postbiotic metabolites constituting the active substance according to the invention.

The method according to the invention can also comprise a purification step and/or a decoloration step and/or a deodorization step.

The steps of the methods described above, taken individually, are commonplace in the field of the extraction of active substances from natural raw materials, and a person skilled in the art is able to adjust the reaction parameters based on their general knowledge.

The active substance can then be optionally combined with a support and dried with or without a support (atomization or lyophilization, in particular) so as to be in solid form.

"Culture medium" is understood to refer to any medium comprising at least the nutrients necessary for the growth and multiplication of lactobacilli. Those skilled in the art know that a suitable culture medium comprises carbohydrate nutrients (preferably in the form of oligosaccharides), nitrogenous nutrients (preferably provided in the form of peptides through a yeast extract), and a supply of salts necessary for the buffering capacity of the medium. For example, the culture medium can be that of the publication (De MAN, J. C., ROGOSA, M., and SHARPE, M. E. 1960)).

Cosmetic Use

The active substance according to the invention is particularly effective for cosmetic, non-therapeutic treatment.

In particular, the active substance according to the invention has an effective action, alone or in a cosmetic composition, on healthy skin to enhance the beauty of the skin.

The invention therefore relates to the cosmetic use of an active substance according to the invention or of a cosmetic composition containing same on healthy skin to enhance the beauty of the skin.

The active substance according to the invention is capable of regulating the skin microbiota, improving the integrity and renewal of the epidermal barrier, activating the innate immune defenses, and reducing inflammation and abnormal epidermal proliferation:

with respect to the microbiota: the application of an active substance according to the invention to the skin has no effect on the diversity and distribution of bacterial communities, reflecting the neutrality of the active substance with respect to the skin flora, Increased integrity of the epidermal barrier: the active substance according to the invention activates the mechanisms inherent in the establishment of an effective barrier function. It improves the synthesis of the protein backbone (filaggrin in particular), promotes the cohesion of the epidermis (claudin-4 and desmoglein-1 in particular), and optimizes the formation of lipid cement (expression of enzymes for the synthesis of lipids GBA, ABCA12, FASN in particular). This action results in an improvement of the barrier function by 71%. This effect has also been observed in volunteers.

Renewal of the activated barrier: the rate of renewal of the epidermis is accelerated by virtue of the application of the active substance according to the invention.

Optimized immunity: the active substance according to the invention allows for improvement of the immune barrier, particularly by increasing the expression of the danger receptor TLR2 and of the antimicrobial peptide HBD2.

Reduced inflammation and abnormal epidermal proliferation: the active substance according to the invention makes it possible to reduce the secretion of IL-17 by T helper 17 lymphocytes.

The invention therefore also relates to the specific cosmetic use of the active substance as described in the present application to:

regulate the balance of skin flora, and/or reinforce the integrity of the skin barrier, and/or activate epidermal renewals, and/or energize the innate immune defenses.

The active substance according to the invention can be used to:

improve the glow of the skin, and/or enhance the radiance of the skin, and/or increase the hydration of the skin.

Advantageously, the active substance according to the invention makes it possible to enhance the quality of skin suffering from dryness by acting on the various levers responsible for epidermal homeostasis: hydration is improved and the radiance of the complexion revived, even in different areas of the body (the hands and face in particular). Thanks to its postbiotic action, the active substance according to the invention improves the integrity and renewal of the epidermal barrier while respecting the balance of the microbial flora.

Cosmetic Composition

The active substance according to the invention is preferably used in compositions, these compositions comprising a cosmetically acceptable medium. The compositions are in different galenical forms, suitable for topical application to the skin.

These compositions can be particularly in the form of oil-in-water emulsions, water-in-oil emulsions, multiple emulsions (water/oil/water or oil/water/oil) which may optionally be microemulsions or nanoemulsions, or in the form of solutions, suspensions, hydrodispersions, aqueous gels or powders. They can be more or less fluid and have the appearance of creams or gels or any other appearance of skin care cosmetics.

They can be compositions comprising at least 0.1% of the liquid active substance according to the invention, preferably between 0.5 and 10% or at least 0.02% of the solid active substance according to the invention, preferably between 0.1 and 2%.

In addition to the active substance, these compositions comprise a physiologically acceptable and preferably cosmetically acceptable medium, i.e., one that does not cause sensations of discomfort that are unacceptable to the user, such as redness, tightness, or tingling.

As an additive, the compositions according to the invention may contain at least one compound selected from:

oils, which can be selected particularly from linear or cyclic, volatile, or non-volatile silicone oils;

waxes such as ozokerite, polyethylene wax, beeswax, or carnauba wax, silicone elastomers, surfactants, preferably emulsifiers, whether non-ionic, anionic, cationic, or amphoteric, co-surfactants such as linear fatty alcohols, thickeners and/or gelling agents, humectants such as polyols like glycerin, dyes, preservatives, fillers,
tighteners,
sequestrants,
perfumes,
and mixtures thereof, without this list being exhaustive.

Examples of such additives are cited particularly in the CTFA Dictionary (*International Cosmetic Ingredient Dictionary and Handbook*, published by the *Personal Care Product Council*).

Of course, a person skilled in the art would take care to select any additional compounds, active or non-active, and the quantity thereof such that the advantageous properties of the mixture are not, or not substantially, altered by the addition envisaged.

These compositions are particularly intended for use on healthy skin, particularly dry and/or lackluster healthy skin, in order to improve the glow of the skin and/or enhance the radiance of the skin and/or increase the hydration of the skin.

The invention thus also relates to a cosmetic (non-therapeutic) method, namely a cosmetic method for treating healthy skin in order to enhance the beauty of the skin, and particularly to improve the glow of the skin and/or enhance the radiance of the skin and/or increase the hydration of the skin, which consists of topical application of a composition comprising an active substance according to the invention to healthy skin.

Preferably, the composition comprising the cosmetic active substance according to the invention is applied at least once a day for at least 15 days.

The following examples and test results are presented below in order to illustrate these cosmetic effects on the quality of the skin, particularly on the properties of the skin.

EXAMPLES

Example 1: Active Substance According to the Invention

The active substance of example 1 is obtained from the bacterium *Lactobacillus arizonensis* and from an extract of jojoba *Simmondsia chinensis*.

Preparation of the jojoba extract: An extract of jojoba cake is produced by enzymatic hydrolysis of a jojoba cake that was previously solubilized in water. This original substrate of *L. arizonensis* is added in a form that the bacteria are able to assimilate.

Culture management: For the cultivation of the bacteria, the culture medium is similar to that described as plant SRM sold by Biokar diagnostics. The jojoba extract is added to this culture medium.

The strain of *L. arizonensis* is thus cultivated in the culture medium described above. The inoculation is adapted to the size of the bioreactor used in terms of volume and growth time.

The culture is carried out under the conditions suitable for the strain. The pH is maintained during growth by adding sodium hydroxide.

The growth is followed by measurement of the absorbance through the addition of soda and by the consumption of glucose.

At harvest, the culture is thermally inactivated for 30 minutes at 80° C., then centrifuged in order to separate the biomass and the supernatant.

The supernatant is used as an active substance after filtration and sterilizing filtration.

The active substance obtained through bioconversion has the following analytical characteristics:

Dry material content of 80 g/L

A carbohydrate content of 3.4 g/L (as determined using the DUBOIS method), or 4% relative to the dry material. The carbohydrate fraction is composed chiefly (67%) of bound sugars containing glucose and galactose and 33% of fructose in free form.

9.9 g/L of proteins (as determined using the Kjeldhal method), or 12% relative to the dry material. The protein fraction is composed of 65% oligopeptides from 243 Da to 2000 Da.

21.5 g/L of ash (determined by weighing the residues resulting from the incineration of the sample at 550° C. in an electric muffle furnace), or 27% of the dry material.

A lactic acid content of 44.6 g/L, or 56% of the dry material.

A Pinnitol content of 500 ppm.

A pH of 5.4.

Example 2: Active Substance According to the Invention in Solid Form

The active substance according to example 2 is obtained from the bacterium *Lactobacillus arizonensis* in the same manner as for example 1. After recovery of the supernatant, it is decolorized, deodorized, concentrated, debacterized, and atomized on a support containing 75% maltodextrin.

The active substance obtained has the following analytical characteristics:

A dry material content of 970 mg/g

A carbohydrate content of 723 mg/g (as determined using the DUBOIS method) or 75% relative to the dry material.

16 mg/g of proteins (as determined using the Kjeldhal method) or 2% relative to the dry material.

89 mg/g of ash (determined by weighing the residues resulting from the incineration of the sample at 550° C. in an electric muffle furnace) or 9% relative to the dry material.

A lactic acid content of 131 mg/g or 14% relative to the dry material.

A Pinnitol content of 1584 ppm.

A pH of 5.5.

Example 3: Non-Inventive Product Obtained with a Non-Specific Substrate for the *Lactobacillus L. Arizonensis* (Sunflower Cake Extract)

The product according to example 3 is obtained from the bacterium *Lactobacillus arizonensis* in the same manner as for example 1 except for the Jojoba extract, which is replaced by an extract of sunflower cake in identical quantities.

The product obtained has the following analytical characteristics:

A dry material content of 79.4 g/L.

A carbohydrate content of 2.1 g/L (as determined using the DUBOIS method), or 3% relative to the dry material.

11.6 g/L of protein by weight of dry material (as determined using the Kjeldhal method), or 15%.

20.4 g/L of ash (determined by weighing the residues resulting from the incineration of the sample at 550° C. in an electric muffle furnace), or 26%.

A lactic acid content of 44.5 g/L, or 56% relative to the dry material.

A pH of 5.6.

Example 4: Non-Inventive Product Corresponding to the Culture Medium Containing the Jojoba Extract The product according to example 4 corresponds to the culture medium of example 1 described above.

The product obtained has the following analytical characteristics

A dry material content of 36.6 g/L.

A carbohydrate content of 8.1 g/L (as determined using the DUBOIS method), or 22% relative to the dry material.

19.0 g/L of protein by weight of dry material (as determined using the LOWRY method), or 52% relative to the dry material.

9.5 g/L of ash (determined by weighing the residues resulting from the incineration of the sample at 550° C. in an electric muffle furnace), or 26% relative to the dry material.

Example 5: Non-Inventive Product Obtained in the Absence of the Specific Substrate for Lactobacilli (without Jojoba)

The product according to example 5 is obtained from the bacterium *Lactobacillus arizonensis* in the same manner as for example 1 except for the culture medium, which does not contain any Jojoba extract.

The active substance obtained has the following analytical characteristics:

A dry material content of 98.9 g/L

A carbohydrate content of 2.6 g/L (as determined using the DUBOIS method), or 3% relative to the dry material. The carbohydrate fraction consists of 51% fructose in free form and 49% bound sugars containing glucose and galactose.

12.8 g/L of protein by weight of dry material (as determined using the LOWRY method), or 13% relative to the dry material.

15.8 g/L of ash (determined by weighing the residues resulting from the incineration of the sample at 550° C. in an electric muffle furnace), or 16% relative to the dry material.

A lactic acid content of 67 g/L, or 68% relative to the dry material.

Example 6: Example of a Healthy Glow Skincare Composition, an Illuminating Treatment for Gently Revealing the Glow of the Skin The composition of this example is a light and slippery treatment with an immediate healthy glow effect by virtue of the pink and gold nacres. Easy to spread, it absorbs quickly, leaving a soft and powdery finish.

Its formula is shown in Table 1.

TABLE 1

| PHASE | INGREDIENTS - INCI | Supplier | % |
|---|---|---|---|
| A | Aqua | — | Q.s. 100 |
|   | Glycerin | — | 2 |
|   | Hydroxyethylcellulose | Ashland/IMCD | 0.5 |
| B | Disodium cetearyl sulfosuccinate | BASF | 0.5 |
|   | Glycol palmitate | Seppic | 2 |
|   | C10-18 Triglycerides | Stéarinerie Dubois | 1 |
|   | Isopropyl myristate | Stéarinerie Dubois | 5 |
|   | Dimethicone | Dow/Univar | 2 |
|   | Triheptanoin | Seppic | 5 |
| C | Butylene glycol | — | 10 |
|   | Titanium dioxide & synthetic fluorophlogopite | SunChemical/Maprecos | 1.5 |
|   | Titanium dioxide & synthetic fluorophlogopite | SunChemical/Maprecos | 1.5 |
| D | Ammonium acryloyldimethyltaurate/VP | Clariant | 0.75 |
| E | ACTIVE SUBSTANCE of example 2 | Silab | 1 |
| F | Citric acid | — | Q.s. pH 5.0-5.5 |

The composition is obtained by implementing the following procedure:

Place A under magnetic stirring and heat to 80° C.
Place B under magnetic stirring and heat to 80° C.
Under rotor-stator, emulsify B in A.
At 40° C., under moderate stirring, add C then D and E
Adjust the pH with F The composition is in the form of a flexible emulsion with a pearly white color and shiny; pH=5.2 with a viscosity (B/5 rpm)=20,000 cPs.

Example 7: Example of Velvet Cream Composition for the Hands

The composition of this example is a nourishing and regenerating cream for the hands. Quick to penetrate, it leaves a comfortable, non-greasy protective film.

The formula of the composition is shown in Table 2.

TABLE 2

| PHASE | INGREDIENTS - INCI | Supplier | % |
|---|---|---|---|
| A | Aqua | — | Q.s. 100 |
|   | Glycerin | — | 2 |
|   | Butylene glycol | — | 3 |
|   | Aqua & sodium hydroxide | — | 0.3 |
| B | Cetearyl alcohol & dicetyl phosphate & ceteth-10 phosphate | Croda | 5 |
|   | PPG-3 benzyl ether myristate | Croda | 5 |
|   | C12-15 alkyl benzoate | Evonik/Adara | 3 |
|   | Dimethicone | Dow/Univar | 2 |
|   | *Simmondsia chinensis* seed oil (and) hydrogenated vegetable oil | Sophim | 2 |
|   | Cera alba | Baerlocher | 2 |
| C | Hydroxyethyl acrylate/sodium acryloyldimethyl taurate copolymer & polyisobutene & PEG-7 trimethylolpropane coconut ether | Seppic | 2 |
| D | ACTIVE SUBSTANCE of example 2 | Silab | 1 |

The composition is obtained by implementing the following procedure:
Place A under magnetic stirring and heat to 80° C.
Place B under magnetic stirring and heat to 80° C.
Under rotor-stator, emulsify B in A
At 40° C., under moderate stirring, add C then D.
The composition is in the form of a thick white and shiny emulsion, with a pH=6.0-6.3 and a viscosity (D/5 rpm)=145,000 cPs.

Example 8: Example of Composition in the Form of a Foot Cream

The composition of this example is a comforting cream with a rich and creamy texture. Quickly absorbed, it imparts softness and suppleness to the skin of the feet without leaving a greasy film.
The formula of the composition is shown in Table 3.

TABLE 3

| PHASE | INGREDIENTS - INCI | Supplier | % |
|---|---|---|---|
| A | Aqua | — | Q.s. 100 |
|   | Butylene glycol | — | 5 |
| B | Cetearyl alcohol & ceteareth-33 | Seppic | 5 |
|   | Isocetyl stearoyl stearate | Stéarinerie Dubois | 3 |
|   | Caprylic capric triglycerides | Stéarinerie Dubois | 7 |
|   | Coco-caprylate/caprate | Stéarinerie Dubois | 4 |
|   | Dimethicone | Dow/Univar | 2 |
| C | Hydroxyethyl acrylate/sodium acryloyldimethyl taurate copolymer & polyisobutene | Seppic | 2 |
| D | ACTIVE SUBSTANCE example 1 | Silab | 2.5 |

The composition can be obtained by carrying out the following procedure:
Place A under magnetic stirring and heat to 80° C.
Place B under magnetic stirring and heat to 80° C.
Under rotor-stator, emulsify B in A
At 40° C., under moderate stirring, add C then D
The composition is in the form of a thick, white, and shiny emulsion, with a pH=5.3-5.5 and a viscosity (D/5 rpm)=100,000-110,000 cPs.

Example 9: Example of Composition in the Form of Body Milk

The composition of this example is a nourishing, lipid-replenishing, and protective body milk. Easy to spread and quick to penetrate, it leaves the skin soft and silky all day long.
The formula of the composition according to the invention is presented in Table 4.

TABLE 4

| PHASE | INGREDIENTS - INCI | Supplier | % |
|---|---|---|---|
| A1 | Aqua | — | Q.s. 100 |
|   | Glycerin | — | 2 |
|   | Butylene glycol | — | 5 |
|   | Acacia Senegal gum & xanthan gum | Seppic | 0.5 |
| A2 | Potassium cetyl phosphate | DSM/IES | 2 |

TABLE 4-continued

| PHASE | INGREDIENTS - INCI | Supplier | % |
|---|---|---|---|
| B | Isocetyl stearoyl stearate | Stéarinerie Dubois | 2 |
|   | Coco-caprylate/caprate | Stéarinerie Dubois | 5 |
|   | Dimethicone | Dow/Univar | 2 |
|   | Tocopherol & *Heliantus annus* seed oil | BTSA/CQ Masso | 0.05 |
|   | *Butyrospermum parkii* (shea) butter | Sophim | 2 |
|   | Cera alba | Baerlocher | 1 |
| C | Polyacrylate crosspolymer-6 | Seppic | 1 |
| D | ACTIVE SUBSTANCE example 1 | Silab | 2.5 |

The composition can be obtained by carrying out the following procedure:
Place A1 under moderate stirring. Stir until homogenized.
Add A2 to A1 under stirring. Heat to 80° C.
Add A3 to A1+A2 under stirring.
Place B under magnetic stirring and heat to 80° C.
Under rotor-stator, emulsify B in A.
At 40° C., under moderate stirring, add C then D.
The composition is in the form of a flexible white and shiny emulsion, with a pH=6.2 and a viscosity (B/5 rpm)= 16,000 cPs.

Tests Demonstrating the Cosmetic Efficacy of the Invention
In Vitro Tests
Effect of an Active Substance According to the Invention on Epidermal Differentiation/Cohesion
The objective of this study is to evaluate the capacity of an active substance according to the invention to maintain a functional epidermal differentiation/cohesion by stimulating the syntheses of filaggrin, claudin-4, and desmoglein-1.
The skin barrier protects the body against external constraints, whether of a physical, chemical, or environmental nature. It also helps fight against dehydration by limiting the diffusion of water out of the body. A multitude of protein components is essential for the establishment of this barrier function, such as:
filaggrin, which plays a major role in the formation of the stratum corneum, the last barrier of our body against the external environment. It also ensures hydration thereof thanks to the amino acids that result from its proteolysis and constitute a large part of the "natural hydration factors;"
claudin, which is one of the main constituents of tight junctions: complex structures that establish a real intercellular barrier in the upper layers of the epidermis, limiting and regulating the passage of solutes in this space;
desmoglein-1, which is an anchoring protein belonging to the family of the desmosomal cadherins. It ensures cohesion between the adjacent keratinocytes, thus forming a transcellular network.
Two studies were carried out: a first study by immuno-histofluorescence on normal SILABSKIN® RE reconstructed epidermises subjected to water stress, and a second study by immunostaining on normal human keratinocytes subjected to a dry environment. Study of reconstructed epidermises.
The procedure is described below.
I. Culturing and Processing of SILABSKIN® RE:
On D0: Normal human keratinocytes are seeded on inserts and then incubated at 37° C. in an atmosphere containing 5% CO2.
The culture medium is changed regularly.

After several days of culturing: water stress is applied (environment at 40% relative humidity) in order to induce dehydration. Control reconstructed epidermises are left in an environment saturated with humidity (82% relative humidity).

The SILABSKIN® RE are treated for 24 hours topically with the active substance of example 1 at 0.25% and 0.50% (V/V).

After one day, the SILABSKIN® RE are recovered, fixed, dehydrated, and enclosed in paraffin. Sections are then made using a microtome.

II. Analysis of the Synthesis of Filaggrin, Claudin-4, and Desmoglein-1 by Immunohistofluorescence:

By means of primary antibodies:
  Anti-filaggrin antibody
  Anti-claudin-4 antibody
  Anti-desmoglein-1 antibody
Secondary antibodies: coupled with Alexa Fluor® 488

III. Reading Immunostaining:

Viewing is performed using a microscope coupled to an image analysis system. The rate of the various synthesized markers is proportional to the intensity of green fluorescence present on the reconstructed epidermises. Quantitative analysis of the images was performed using software. The results are expressed in arbitrary units (AU). The results are shown in Table 5 (Capacity of an active substance according to the invention to restore the synthesis of filaggrin, claudin-4, and desmoglein-1 in SILABSKIN® RE subjected to water stress).

nocytology on normal human keratinocytes subjected to a dry environment. The procedure is as follows:

Normal human keratinocytes are seeded and incubated at 37° C. in an atmosphere containing 5% $CO_2$ for several days.

Then, the keratinocytes are either incubated at 37° C. under 5% CO2 in an environment of 40% relative humidity in order to mimic a dry environment, or they are kept in an environment that is saturated with humidity (82% relative humidity) in the presence or absence of the products of examples 1 to 5 or in the presence of a sodium lactate solution at 45 g/L (pH 5.4).

After 24 h, immunostaining is performed using an anti-filaggrin primary antibody and a coupled secondary antibody, Alexa Flor® 488.

The nuclei are stained with a DAPI solution.

Viewing is performed using an IX 70 microscope (Olympus) coupled to an image analysis system (NIS-Elements software, Nikon).

The synthesized filaggrin is proportional to the intensity of green fluorescence present on the keratinocytes. A quantitative analysis of the images was performed using Matlab® software. The results are expressed in arbitrary units (AU) in Table 6 (Effect of the various examples on their ability to restore the synthesis of filaggrin in human keratinocytes subjected to water stress).

TABLE 5

|  | Synthesis of filaggrin (AU) | Ability to restore filaggrin synthesis (%) | Synthesis of claudin-4 (AU) | Ability to restore claudin-4 synthesis (%) | Synthesis of desmoglein-1 (AU) | Ability to restore desmoglein-1 synthesis (%) |
|---|---|---|---|---|---|---|
| SILABSKIN ® RE normal |
| Control | 1144 |  | 213 |  | 648 |  |
| Example 2 0.50% | 1146 |  | 224 |  | 747 |  |
| SILABSKIN ® RE - water stress |
| Control | 862 |  | 154 |  | 498 |  |
| Example 2 0.25% | 1067 | 73 | 185 | 53 | 644 | 97 |
| Example 2 0.50% | 1138 | 98 | 211 | 97 | 742 | 163 |

These results show that, when subjected to water stress, SILABSKIN® RE exhibits an alteration in epidermal differentiation and cohesion that is characterized by a significant reduction in the synthesis of filaggrin, claudin-4, and desmoglein-1. In addition, it is noted that, as tested at 0.50% on this model, the active substance according to the invention is capable of significantly restoring the synthesis of:
  filaggrin: +98%;
  claudin-4: +97%;
  desmoglein-1: +163%.

Thus, the use of an active substance according to the invention makes it possible to restore the epidermal differentiation process in order to obtain a cohesive structure. The second study on the keratinocytes makes it possible to compare the effect of the products of the various examples 1 to 5. To do this, their capacity to restore the synthesis of filaggrin by human keratinocytes subjected to a dry environment is compared. This study was carried out by immu-

TABLE 6

|  | Synthesis of filaggrin (AU) | Ability to restore filaggrin synthesis (%) |
|---|---|---|
| Normal keratinocytes |
| Control | 3524 |  |
| Keratinocytes - water stress |
| Control | 722 |  |
| Example 1 at 0.5% | 3839 | 111 |
| Example 2 at 0.2% | 3526 | 100 |
| Example 3 at 0.5% | 609 | 0 |
| Example 4 at 0.5% | 653 | 0 |
| Example 5 at 0.5% | 700 | 0 |
| Sodium lactate (45 g/L) at 0.5% | 909 | 7 |

These results show that only the active substances according to the invention of examples 1 and 2 corresponding to the invention enable restoration of the synthesis of filaggrin by cultures of human keratinocytes subjected to water stress.

The product of example 3—that is, the product resulting from the bioconversion of the sunflower extract by *lactobacillus*—does not enable the restoration of filaggrin synthesis. Therefore, the molecules acting on this synthesis are not present in the supernatant of the *lactobacillus* culture cultivated in a culture medium supplemented with a substrate other than that of said *lactobacillus*.

The product of example 4—that is to say the culture medium specific for *lactobacillus*—does not restore filaggrin synthesis. The molecules acting on this synthesis are therefore not contained in the *lactobacillus* culture medium.

The product of example 5—that is, the product resulting from the culture of *lactobacillus* in the "conventional" culture medium—does not restore filaggrin synthesis. Therefore, the molecules acting on this synthesis are not present in the supernatant of a *lactobacillus* culture in a "conventional" culture medium.

The sodium lactate solution at the same concentration as that of example 1 does not restore filaggrin synthesis. Sodium lactate is therefore not responsible for the synthesis of filaggrin in keratinocyte cultures.

Effect of an Active Substance According to the Invention on the Major Actors in the Synthesis and Secretion of Epidermal Lipids The objective of this study is to evaluate the capacity of an active substance according to the invention to restore the expression of various actors essential for the synthesis of epidermal lipids.

Intercorneocyte lipids play a fundamental role in the skin barrier function. Essentially synthesized by keratinocytes, the lipid matrix has a specific composition and organization that makes it possible to ensure the tightness of the stratum corneum by regulating the flow of electrolytes from the inside of the body to the outside and vice versa. Their synthesis and secretions involve various actors, including:

β-glucosylceramidase (GBA) is a lysosomal protein that catalyzes the production of ceramides: major lipids essential for the stratum corneum;

fatty acid synthase (FASN) is an enzyme that is necessary for the synthesis of free fatty acids in intercorneocyte cement;

ATP binding cassette subfamily A member 12 (ABCA12) is a key molecule in the generation, transport, and secretion of lipids. It is also involved in keratinocyte differentiation.

This study was carried out by PCR on normal SILABSKIN® RE reconstructed epidermises subjected to water stress.

The procedure is described below:

Culturing and treatment of SILABSKIN® RE: first, the reconstructed epidermises are cultivated and treated.

Normal human keratinocytes are seeded on inserts and then incubated at 37° C. in an atmosphere containing 5% CO2.

The culture medium is changed regularly.

After several days of cultivation, the SILABSKIN® RE are either incubated at 37° C. in an environment of 40% relative humidity for several hours in order to induce dehydration, or they are left in an environment saturated with humidity (82% relative humidity)

Then, the SILABSKIN® RE are treated topically with the active substance of example 1 at 0.25% and 0.50% (V/V)

Finally, the SILABSKIN® RE are recovered and the total RNAs extracted.

II. Analysis of the Expression of GBA, FASN, and ABCA12 by Quantitative PCR:

The RNAs were reverse-transcribed, and the complementary DNAs obtained were analyzed by the quantitative PCR technique. The mRNAs of the RPS18 and GUSB proteins, internal reference controls, were analyzed in parallel with the mRNAs of GBA, FASN, and ABCA12.

The quantification of the incorporation of fluorescence (SYBR Green) is measured continuously using a thermal cycler. The RQ (relative quantification) analysis is performed using software.

The results are shown in Table 7 (Capacity of an active substance according to the invention to restore the expression of ABCA12, GBA, and FASN in SILABSKIN® RE subjected to water stress).

TABLE 7

|  | ABCA12 expression (%) | Ability to restore ABCA12 expression (%) | GBA expression (%) | Ability to restore GBA expression (%) | FASN expression (%) | Ability to restore FASN expression (%) |
| --- | --- | --- | --- | --- | --- | --- |
| SILABSKIN ® RE normal | | | | | | |
| Control | 100 | | 100 | | 100 | |
| Example 1 at 0.50% | 153 | | 144 | | 143 | |
| SILABSKIN ® RE - water stress | | | | | | |
| Control | 73 | | 65 | | 77 | |
| Example 1 at 0.25% | 130 | 211 | 135 | 200 | 125 | 209 |
| Example 1 at 0.50% | 139 | 244 | 169 | 297 | 137 | 261 |

These results show that, when subjected to water stress, SILABSKIN® RE exhibits a significant decrease in synthetic enzymes and transport proteins for intercorneocyte lipids. It can be seen that, when tested at 0.50% on this model, the active substance according to the invention significantly restores the expression of:

ABCA12: +244%;

GBA: +297%;

FASN: +261%.

By acting favorably on the major actors in the biology of epidermal lipids, the active substance according to the invention activates the formation of lipid cement, an element that is essential for the formation of a functional barrier.

Effect of an Active Substance According to the Invention on the Barrier Function The objective of this study is to evaluate the capacity of an active substance according to the invention to limit the Insensitive Water Loss (IWL) of a model of SILABSKIN® RE reconstructed epidermises subjected to water stress.

Insensitive water loss is the passive diffusion of water through the stratum corneum. Its measurement makes it possible to assess the integrity of the epidermal barrier function. When this is altered, the flow of water to the outside environment intensifies, increasing the value of the IWL.

This study was carried out by measuring the IWL using a Tewameter® on normal SILABSKIN® RE reconstructed epidermises subjected to water stress.

The procedure is described below:

I. Culturing and Processing of SILABSKIN® RE:

normal human keratinocytes are seeded on inserts and then incubated at 37° C. in an atmosphere containing 5% CO2.

the culture medium is changed regularly.

After several days of cultivation, the SILABSKIN® RE are either incubated at 37° C. under 5% CO2 in an environment at 40% relative humidity for several hours in order to induce dehydration, or they are left in a saturated environment with humidity (82% relative humidity).

Then, the SILABSKIN® RE are treated for 24 hours topically with the active substance of example 1 at 0.25% and 0.50% (V/V).

Finally, the SILABSKIN® RE are dried and incubated for one hour at room temperature. The IWL is measured using a Tewameter® CM 820 (Courage & Khazaka).

The results are shown in Table 8 (Ability of an active substance according to the invention to limit insensitive water loss from SILABSKIN® RE subjected to water stress).

TABLE 8

| | IWL (g/h/m²) | Ability to limit insensitive water loss (%) |
|---|---|---|
| SILABSKIN ® RE normal | | |
| Control | 10.74 | |
| Example 2 at 0.50% | 11.32 | |
| SILABSKIN ® RE - water stress | | |
| Control | 13.77 | |
| Example 2 at 0.25% | 12.62 | 38% |
| Example 2 at 0.50% | 11.62 | 71% |

Subject to water stress, SILABSKIN® RE exhibits a significant increase of 28% in insensitive water loss.

When tested at 0.5% on this model, the active substance according to the invention significantly limited epidermal dehydration by 71%.

By retaining a functional skin barrier, the active substance according to the invention limits the effects of epidermal dehydration.

Effect of an Active Substance According to the Invention on the Innate Immune Defenses The objective of this study is to evaluate the capacity of an active substance according to the invention (example 1) to regulate the innate immune defenses of the skin. For this, the expression of defensins 2 (HBD2) and of toll-like receptor 2 (TLR2) was measured on a model of SILABSKIN® RE reconstructed epidermis in water stress.

One of the primary functions of the skin is to form an effective barrier against pathogenic microbes with which it is continually confronted. Keratinocytes are the first sentinels of this immune barrier. They have receptors, including TLR2, that enable them to detect and distinguish between microorganisms resident in commensal flora and transient pathogenic microorganisms. To neutralize and eliminate them, keratinocytes synthesize antimicrobial peptides such as HBD2. The latter are widely expressed by keratinocytes and are characterized by broad-spectrum antimicrobial action.

This study was carried out by QPCR on normal SILABSKIN® RE reconstructed epidermises subjected to water stress.

The procedure is described below.

I. Culturing and Processing of SILABSKIN® RE:

Normal human keratinocytes are seeded on inserts and then incubated at 37° C.

The culture medium is changed regularly.

SILABSKIN® RE are either incubated at 37° C. under 5% CO2 in an environment of 40% relative humidity for several hours in order to induce dehydration, or they are left in an environment saturated with humidity (82% relative humidity)

Then, the SILABSKIN® RE are treated for 24 hours topically with the active substance of example 1 at 0.25% and 0.50% (V/V) and either incubated at 37° C. under 5% CO2 in 40% relative humidity environment or left in an environment saturated with humidity (82% relative humidity).

Finally, the SILABSKIN® RE are recovered and the total RNAs extracted.

II. Analysis of HBD2 and TLR2 Expression by Quantitative PCR

The RNAs were reverse-transcribed, and the complementary DNAs obtained were analyzed by the quantitative PCR technique. The mRNAs of the RPS18 and GUSB proteins, internal reference controls, were analyzed in parallel with the mRNAs of HBD2 and TLR2.

The quantification of the incorporation of fluorescence (SYBR Green) is measured continuously using a thermal cycler. The RQ (relative quantification) analysis is performed using software.

The results are shown in Table 9 (Capacity of an active substance according to the invention to restore the expression of HBD2 and TLR2 by SILABSKIN® RE subjected to water stress).

TABLE 9

| | HBD2 expression (%) | Ability to restore HBD2 expression (%) | TLR2 expression (%) | Ability to restore TLR2 expression (%) |
|---|---|---|---|---|
| SILABSKIN ® RE normal | | | | |
| Control | 100 | | 100 | |
| Example 2 at 0.50% | 113 | | 144 | |
| SILABSKIN ® RE - water stress | | | | |
| Control | 43 | | 67 | |
| Example 2 at 0.25% | 62 | 33 | 128 | 185 |
| Example 2 at 0.50% | 100 | 100 | 147 | 242 |

These results show that, when subjected to water stress, SILABSKIN® RE exhibit a significant decrease in innate antibacterial defenses. It can be seen that, when tested at 0.50% on this model, the active substance according to the invention significantly restores the expression of:

HBD2: +100%,
TLR2: +242%

The use of an active substance according to the invention thus limits the deleterious effects of water stress on the skin immune barrier.

Effect of the Active Substance According to the Invention on the Secretion of IL-17 by TT Helper 17 Lymphocytes Interleukin 17 (IL-17) is a cytokine produced by T helper 17 (Th17L) lymphocytes that has effects on the biology of the epidermis. It causes inflammation and abnormal epidermal proliferation. In particular, IL-17 is implicated in psoriasis.

This study was carried out in order to demonstrate the potential activity of the active substance according to the invention on the secretion of IL-17 by Th17L.

The procedure is as follows:

Native T lymphocytes are isolated from mononuclear cells of peripheral blood and cultured in a medium containing a mixture allowing their differentiation into Th17L. The cells are then incubated at 37° C. in an atmosphere containing 5% CO2.

After several days, the culture medium is removed and replaced by a medium containing a mixture allowing differentiation in the presence or absence of cyclosporin or of the active substance according to example 2 at 0.1%.

After several hours, the supernatant is collected and frozen at −80° C.

The IL-17 are assayed by ELISA.

The results are summarized in table 10 below:

TABLE 10

|  | IL-17 secretion (pg/mL) | Ability to limit IL-17 secretion (%) |
| --- | --- | --- |
| Control | 1497 |  |
| Cyclosporine 1 µg/mL | 567 | −62 |
| Active substance example 2 at 0.1% | 865 | −42 |

When placed in a medium that induces their differentiation, native T lymphocytes differentiate into Th17L. This process leads to an increase in the production of IL-17. Tested at 0.1% on Th17 lymphocytes, the active substance according to the invention limits the secretion of IL-17 by 42%.

Effect of an Active Substance According to the Invention on the Expression of Dermal Markers The objective of this study is to evaluate the effect of the active substance according to example 1 on increasing the expression of mRNA encoding for the main collagens of the dermis: collagen I and collagen III, as well as the main collagens of the dermo-epidermal junction: collagen IV and collagen VII, and for the enzyme HAS-2 (hyaluronan synthase 2) involved in the synthesis of hyaluronic acid.

This study was carried out by PCR on normal human fibroblasts.

The procedure of the study is described below:

I. Culturing and Treatment of Fibroblasts:
Normal human fibroblasts are inoculated into a culture medium and then incubated at 37° C. in an atmosphere containing 5% CO2.

Then, the fibroblasts are cultured in the presence or absence of the active substance of example 1 at 0.5% and 1% (V/V).

TGF-β at 10 ng/mL is used as a positive control. Finally, the fibroblasts are recovered and the total RNAs extracted.

II. Analysis of the Expression of Coll I, Coll III, Coll IV, Coll VII and HAS-2 by Quantitative PCR:

The RNAs were reverse-transcribed, and the complementary DNAs obtained were analyzed by the quantitative PCR technique. The mRNAs of the RPS18 protein, internal reference control, were analyzed in parallel with the mRNAs of Coll I, Coll III, Coll IV, Coll VII and HAS-2.

The quantification of the incorporation of fluorescence (SYBR Green) is measured continuously using a thermal cycler. The RQ (relative quantification) analysis is performed using software.

The results are shown in Tables 11, 12, and 13 below.

TABLE 11

|  | Collagen I | | Collagen III | |
| --- | --- | --- | --- | --- |
|  | Expression (%) | Efficacy/control (%) | Expression (%) | Efficacy/control (%) |
| Control | 100 |  | 100 |  |
| Example 1 at 0.5% | 114 | +14% | 115 | +15% |
| Example 1 at 1.0% | 122 | +22% | 130 | +30% |
| TGF-β 10 ng/mL | 226 | +126% | 139 | +39% |

TABLE 12

|  | Collagen IV | | Collagen VII | |
| --- | --- | --- | --- | --- |
|  | Expression (%) | Efficacy/control (%) | Expression (%) | Efficacy/control (%) |
| Control | 100 |  | 100 |  |
| Example 1 at 0.5% | 114 | +14% | 107 | +7% |
| Example 1 at 1.0% | 126 | +26% | 121 | +21% |
| TGF-β 10 ng/mL | 318 | +218% | 334 | +234% |

TABLE 13

|  | HAS-2 | |
| --- | --- | --- |
|  | Expression (%) | Efficacy/control (%) |
| Control | 100 |  |
| Example 1 at 0.5% | 127 | +27% |
| Example 1 at 1.0% | 134 | +34% |
| TGF-β 10 ng/mL | 78 |  |

These results show that the active substance according to the invention significantly increases the expression of dermal markers. Thus, the active substance according to the invention increases the expression of mRNA encoding for collagen I by 22%, collagen III by 30%, collagen IV by 26%, collagen VII by 21%, and for the enzyme HAS-2 (hyaluronan synthase 2) by 34%.

In Vivo Tests

The active substance of example 2 was formulated in a single formula in order to conduct all of the in vivo studies, both on Caucasian and Asian panels. The formula is described in Table 14.

TABLE 14

| | |
|---|---|
| Isononyl isononanoate (Lanol 99, Seppic) | 5.0 |
| Behenyl alcohol/arachidyl glucoside/arachidyl alcohol (Montanov 202, Seppic) | 3.0 |
| Active substance according to the invention - example 1 | 1 |
| Cetearyl alcohol/cetearyl glucoside (Montanov 68, Seppic) | 2.0 |
| Preservatives | 1.0 |
| Polyacrylamide/C13-14 isoparaffin/Laureth-7 (Sepigel 305, Seppic) | 0.3 |
| Water | q.s. 100 |

Demonstration of the Effect of the Active Substance According to the Invention on the Skin Microbiota The objective of this study is to evaluate, in vivo, the effect of an active substance according to the invention formulated at 1% in emulsion on the skin microbiota in comparison with the placebo after 28 days of application.

This study was carried out on 18 healthy Caucasian volunteers, aged 32 to 52 years (average age 43±6 years) and presenting dry skin on the hands and face. The volunteers applied the formula containing the active substance according to the invention and the placebo to respective halves of their face in the morning and evening.

The influence of the active substance according to the invention on the cutaneous microbiota was measured by sequencing the V1-V2 variable regions of the gene encoding for 16S ribosomal RNA (16S rDNA), which is common to all bacteria, using the MiSeq® system (Illumina). The skin microbiota on the forehead was sampled and analyzed.

The parameters analyzed are:
alpha-diversity, which reflects the diversity within the sample;
taxonomy, which assesses the composition and distribution of bacterial communities in their relative abundance. In this case, the analysis was conducted at the gender level.

A summary of the results corresponding to the effect of the active substance according to the invention, formulated at 1% in emulsion, on the alpha-diversity of the skin microbiota, as indicated by the Shannon index, in Caucasian volunteers is described as follows:

TABLE 15

| | D 0 | D 28 |
|---|---|---|
| Shannon index | 1.58 | 1.75 |

A summary of the results corresponding to the effect of the active substance according to the invention, formulated at 1% in emulsion, on the distribution of bacterial communities at the level of the 10 major genera after 28 days of twice-daily application is presented as follows:

TABLE 16

| | Relative abundance (%) | |
|---|---|---|
| | D 0 | D 28 |
| Acinetobacter | 0.9% | 0.9% |
| Anaerococcus | 0.4% | 0.7% |
| Corynebacterium | 4.9% | 5.4% |
| Cutibacterium | 57.1% | 54.1% |

TABLE 16-continued

| | Relative abundance (%) | |
|---|---|---|
| | D 0 | D 28 |
| Enhydrobacter | 1.4% | 2.2% |
| Haemophilus | 0.2% | 0.4% |
| Paracoccus | 0.3% | 0.4% |
| Prevotella | 0.3% | 0.4% |
| Staphyloccocus | 20.3% | 20.7% |
| Streptococcus | 1.2% | 1.4% |

Under the conditions of this study, after 28 days of treatment, the active substance according to the invention, formulated at 1%, does not disturb the microbiota of skin suffering from dryness (no significant effect—neither on diversity nor on the composition and distribution of the skin microbiota).

Effect of an Active Substance According to the Invention on the Skin Barrier

The objective of this study is to evaluate, in vivo, the effect of an active substance according to the invention formulated at 1% in emulsion on the skin barrier in comparison with placebo.

Caucasian Panel:
Composed of 18 healthy volunteers, aged 32 to 52 years (average age 43±6 years), presenting dry skin on the hands and face, having applied the formula containing the active substance according to the invention and the placebo to respective sides of their face in the morning and evening.

Asian Panel:
Composed of 31 healthy volunteers, aged 20 to 64 years (average age 44±14 years), presenting dry skin on the face, having applied the formula containing the active substance according to the invention and the placebo to respective sides of their face in the morning and evening.

The capacity of the active substance according to the invention to improve the quality of the skin barrier was evaluated according to the following methods:
measurement of insensitive water loss (IWL) on Caucasian and Asian panels at the cheeks with the aid of a Tewameter® (Courage & Khazaka);
determination of the amount of epidermal lipids on a Caucasian panel from acquisitions made at the cheeks by Raman microspectroscopy (Horiba).

A summary of the results corresponding to the effect of the active substance according to the invention formulated at 1% in emulsion on the IWL of Caucasian and Asian volunteers is presented as follows:

It can be seen that, after 28 days of twice-daily application, and in comparison with placebo, the active substance according to the invention, formulated at 1% in emulsion, improves the barrier function by reducing the insensitive water losses in the face:
15.1% for the Caucasian panel (p=0.0005), effect observed in 83% of volunteers;
20.9% in Asian volunteers (p<0.001). This effect was observed in 87% of them.

A summary of the results corresponding to the effect of an active substance according to the invention, formulated at 1% in emulsion, on the amount of epidermal lipids of Caucasian volunteers is presented as follows:

After 28 days of twice-daily application to the face, and in comparison to placebo, the active substance according to the invention, formulated at 1% in emulsion, improves the barrier function by significantly increasing the quantity of lipids in the stratum corneum by 6.1% (p=0.0022). This effect is observed in 67% of volunteers.

Effect of an Active Substance According to the Invention on Cell Renewal

The objective of this study is to evaluate, in vivo, in comparison with placebo, the capacity of an active substance according to the invention formulated at 1% in emulsion to promote epidermal renewal.

This study was carried out on 14 healthy Caucasian volunteers, aged 28 to 52 years (average age 43±8 years) and presenting dry skin on the hands and face. The volunteers applied the formula containing the active substance according to the invention and the placebo, respectively, to the inside of their forearms in the morning and evening.

The capacity of the active substance according to the invention to improve cell renewal was evaluated on the basis of photographs taken of the inner surface of the forearms using a dermatoscope.

A summary of the results corresponding to the effect of the active substance according to the invention, formulated at 1% in emulsion, on the cell renewal of Caucasian volunteers is presented as follows:

After 14 days of twice-daily application, and in comparison with placebo, the active substance according to the invention, formulated at 1% in emulsion, accelerates the cell renewal of the skin by reducing more quickly the parameter $b^*$, which is representative of the melanin yellow color. Thus, with the active substance according to the invention, the renewal rate is increased by more than 20% (gain of 3 days over 14 days).

Cosmetic Benefits of an Active Substance According to the Invention

The objective of this study is to evaluate, in vivo, the effect of an active substance according to the invention, formulated at 1% in emulsion, on the quality of the skin in comparison with the placebo after 28 days of application.

Caucasian panels (with dry skin on the hands and face):
Study of the face: panel composed of 18 healthy volunteers, aged 32 to 52 years (average age 43±6 years), having applied the formula containing the active substance according to the invention and the placebo to respective halves of their face in the morning and evening.
Study of the hands: panel composed of 19 healthy volunteers, aged 26 to 52 years (average age 43±7 years), having applied the formula containing the active substance according to the invention and the placebo 4 times a day to the back of their hands.
Asian panel (with dry skin on the hands): Composed of 31 healthy volunteers, aged 20 to 64 years (average age 44±14 years), having applied the formula containing the active substance according to the invention and the placebo to respective halves of their face in the morning and evening.

The capacity of the active substance according to the invention to improve the quality of the skin was evaluated according to the following methods:
measurement of the hydration rate using a Corneometer® (Courage & Khazaka) on the hands in a Caucasian panel and on the cheeks in an Asian panel;
observation of skin dryness on the hands on a Caucasian panel using a dermatoscope;
evaluation of radiance of the complexion by clinical scoring on a Caucasian and Asian panel;
observation of the radiance of the complexion in digital photographs in a Caucasian and Asian panel;
sampling and analysis of the skin microbiota from the forehead in a Caucasian panel.

A summary of the results corresponding to the moisturizing effect of an active substance according to the invention formulated at 1% in emulsion is presented as follows:

After 28 days of twice-daily application, and in comparison to placebo, the active substance according to the invention, formulated at 1% in emulsion, significantly increases the hydration of the skin:
on the hands of Caucasian volunteers by 16.2% (p=0.0039). This effect is observed in 67% of volunteers.
on the face of Asian volunteers by 15.8% (p<0.001), an effect that was observed in 87% of them.

A summary of the results corresponding to the effect of the active substance according to the invention, formulated at 1% in emulsion, on the radiance of the complexion, evaluated by experts, in Caucasian volunteers and in Asian volunteers is presented as follows:

After 28 days of twice-daily application, and in comparison with placebo, the active substance according to the invention, formulated at 1% in emulsion, improves the radiance of the complexion of Caucasian and Asian volunteers.

In Caucasian volunteers, the active substance according to the invention:
significantly increases skin radiance (+7.4%, p 0.0023), the pink color representative of a fresh complexion (+14.7%, p=0.0077), as well as the healthy-glow effect (+6.4%, p=0.0147).
significantly decreases olive color (−9.2%, p=0.0232)

In Asian volunteers, the active substance according to the invention significantly increases the radiance of the skin (+13.9% p=0.000), the uniformity of the complexion (+6.0%, p=0.025), and skin hydration (+7.0%, p=0.014).

The use of an active substance according to the invention on healthy skin therefore improves the beauty of the skin, particularly in terms of its radiance and hydration.

The invention claimed is:

1. A cosmetic active substance, characterized in that it is the product obtained through bioconversion by of *Simmondsia chinensis* by *Lactobacillus arizonensis*.

2. The cosmetic active substance according to claim 1, characterized in that it is obtained from a supernatant obtained through bioconversion by of *Simmondsia chinensis* by *Lactobacillus arizonensis*.

3. The cosmetic active substance according to claim 1, characterized in that it is a supernatant obtained through bioconversion by of *Simmondsia chinensis* by *Lactobacillus arizonensis*.

4. The cosmetic active substance according to claim 1, characterized in that it comprises sugars.

5. The cosmetic active substance according to claim 1, characterized in that a carbohydrate fraction of the active substance comprises polysaccharides and oligosaccharides containing glucose, galactose, and fructose.

6. The active substance according to claim 1, characterized in that it comprises at least one cyclic polyol.

7. The cosmetic active substance according to claim 1, characterized in that it comprises at least pinitol.

8. The cosmetic active substance according to claim 1, characterized in that it comprises proteins and/or minerals and/or lactic acid.

9. A cosmetic composition, comprising at least 0.1 wt. % of an active substance according to claim 1.

10. The cosmetic composition according to claim 1, characterized in that it is in the form of a cream or gel.

11. The active substance according to claim 1, characterized in that it is in powder form.

12. A method for obtaining an active substance according to claim 1, characterized in that it comprises the following steps:
Culturing of *Lactobacillus arizonensis* in a culture medium supplemented with *Simmondsia chinensis*;
Stopping cultivation through thermal inactivation;
Separating a biomass from a supernatant;
Filtering the supernatant.

13. The method according to claim 12, characterized in that it also comprises a purification step and/or a decoloration step and/or a deodorization step and/or an atomization step.

14. A method for cosmetic treatment, consisting of using the cosmetic active substance according to claim 1 on healthy skin to improve the beauty of the skin.

15. A method for cosmetic treatment, consisting of using the cosmetic composition according to claim 9 on healthy skin in order to improve the beauty of the skin.

16. A method for cosmetic treatment, consisting of using the cosmetic composition according to claim 9 on healthy skin for improving the glow of the skin and/or enhancing the radiance of the skin and/or increasing the hydration of the skin.

17. A method of cosmetic treatment, consisting of applying the cosmetic composition according to claim 9 on healthy skin to regulate the balance of skin flora and/or to reinforce the integrity of skin barrier and/or to activate epidermal renewals and/or to energize innate immune defenses.

18. A method for cosmetic treatment of healthy skin in order to improve the beauty of the skin, characterized in that it consists of applying a composition according to claim 9 to the skin at least once a day.

19. A method for cosmetic treatment of healthy skin in order to improve the beauty of the skin, characterized in that it consists of applying a composition according to claim 10 to the skin at least once a day.

* * * * *